(12) United States Patent
Chen et al.

(10) Patent No.: US 9,351,910 B2
(45) Date of Patent: May 31, 2016

(54) BENEFIT AGENT DELIVERY PARTICLES COMPRISING DEXTRAN

(75) Inventors: Honggang Chen, Shanghai (CN); Christopher Clarkson Jones, Wirral (GB); Xiaoyun Pan, Shanghai (CN); Jinfang Wang, Shanghai (CN)

(73) Assignee: Conopco, Inc., Englewood Cliffs, NJ (US)

(*) Notice: Subject to any disclaimer, the term of this patent is extended or adjusted under 35 U.S.C. 154(b) by 52 days.

(21) Appl. No.: 14/239,558

(22) PCT Filed: Jul. 30, 2012

(86) PCT No.: PCT/EP2012/064897
§ 371 (c)(1),
(2), (4) Date: Feb. 19, 2014

(87) PCT Pub. No.: WO2013/026656
PCT Pub. Date: Feb. 28, 2013

(65) Prior Publication Data
US 2014/0213499 A1    Jul. 31, 2014

(30) Foreign Application Priority Data
Aug. 24, 2011    (WO) ............. PCT/CN2011/001415

(51) Int. Cl.
| | | |
|---|---|---|
| C11D 3/50 | (2006.01) |
| C11D 3/386 | (2006.01) |
| A61K 8/11 | (2006.01) |
| A61K 8/73 | (2006.01) |
| A61K 8/66 | (2006.01) |
| A61Q 5/02 | (2006.01) |
| C11D 3/22 | (2006.01) |
| C11D 17/00 | (2006.01) |
| A61Q 5/12 | (2006.01) |
| A61K 8/02 | (2006.01) |

(52) U.S. Cl.
CPC ............... A61K 8/11 (2013.01); A61K 8/0241 (2013.01); A61K 8/66 (2013.01); A61K 8/73 (2013.01); A61Q 5/02 (2013.01); A61Q 5/12 (2013.01); C11D 3/222 (2013.01); C11D 3/505 (2013.01); C11D 17/0039 (2013.01); A61K 2800/654 (2013.01)

(58) Field of Classification Search
CPC .......... C11D 3/50; C11D 3/505; C11D 3/222; C11D 17/0039; C11D 3/3769; C11D 3/386; A61K 8/11; A61K 8/73; A61K 8/0241; A61K 8/66; A61K 2800/654; A61Q 5/02; A61Q 5/12

See application file for complete search history.

(56) References Cited

U.S. PATENT DOCUMENTS

| | | | |
|---|---|---|---|
| 2,373,863 | A | 4/1945 | Vitalis |
| 2,749,277 | A | 6/1956 | Toulmin |
| 2,994,665 | A | 8/1961 | Reich |
| 3,523,088 | A | 8/1970 | Dean |
| 4,174,305 | A | 11/1979 | Burns |
| 4,464,271 | A | 8/1984 | Munteanu et al. |
| 4,683,073 | A | 7/1987 | Diehl |
| 4,732,639 | A | 3/1988 | Newsom |
| 4,973,417 | A | 11/1990 | Falholt |
| 5,760,154 | A | 6/1998 | Krause et al. |
| 6,132,750 | A | 10/2000 | Perrier |
| 6,191,093 | B1 | 2/2001 | Watson |
| 6,200,351 | B1 | 3/2001 | Schleinig |
| 6,440,169 | B1 | 8/2002 | Elberg |
| 6,517,933 | B1 | 2/2003 | Soane et al. |
| 6,567,698 | B2 | 5/2003 | Herleikson |
| 6,790,814 | B1 | 9/2004 | Marin |
| 7,316,995 | B2 | 1/2008 | Penninger |
| 7,375,072 | B2 | 5/2008 | Penninger |
| 8,211,452 | B2 | 7/2012 | Miksa et al. |
| 8,637,445 | B2 | 1/2014 | Chen |
| 2003/0018361 | A1 | 1/2003 | Herleikson |
| 2004/0142828 | A1* | 7/2004 | Popplewell et al. .......... 510/101 |
| 2005/0273942 | A1 | 12/2005 | Ferguson |
| 2005/0276831 | A1 | 12/2005 | Dihora et al. |
| 2006/0030504 | A1 | 2/2006 | Penninger |
| 2006/0127345 | A1 | 6/2006 | Hilvert |
| 2006/0143835 | A1 | 7/2006 | Carvell |

(Continued)

FOREIGN PATENT DOCUMENTS

| | | |
|---|---|---|
| CA | 2344406 | 3/2000 |
| CN | 1292814 A | 4/2001 |

(Continued)

OTHER PUBLICATIONS

Vesel et al., Improvement of adhesion of fucoidan on polyethylene terephthalate surface using gas plasma treatments, Vacuum, 2011, vol. 85, pp. 1083-1086.

(Continued)

*Primary Examiner* — Brian P Mruk
(74) *Attorney, Agent, or Firm* — Greenberg Traurig, LLP

(57) ABSTRACT

The invention provides a composition comprising a benefit agent delivery particle comprising dextran as a delivery aid. The benefit agent delivery particle may further comprise a non-polysaccharide polymer, preferably an aminoplast polymer. The benefit agent delivery particle may comprise a perfume. The invention also provides a process for the manufacture of the particles in which perfume oil is encapsulated using emulsion polymerization to form core-shell particles, (in the alternative the perfume may be adsorbed later) and, a further polymer layer is formed on the outer surface of the core shell-particles in the presence of the delivery aid.

10 Claims, No Drawings

(56) References Cited

U.S. PATENT DOCUMENTS

| | | | |
|---|---|---|---|
| 2007/0104660 A1 | 5/2007 | Miksa | |
| 2007/0293414 A1* | 12/2007 | Panandiker et al. | 510/515 |
| 2009/0176676 A1 | 7/2009 | Hilvert et al. | |
| 2011/0082066 A1 | 4/2011 | Wrubbel | |
| 2011/0097369 A1 | 4/2011 | Sunder | |
| 2014/0206587 A1 | 7/2014 | Chen et al. | |
| 2014/0213499 A1 | 7/2014 | Chen et al. | |

FOREIGN PATENT DOCUMENTS

| | | |
|---|---|---|
| CN | 101076373 A | 11/2007 |
| CN | 101355922 A | 1/2009 |
| CN | 101956318 A | 1/2011 |
| DE | 1054638 | 4/1959 |
| DE | 3504450 A1 | 8/1986 |
| DE | 19942581 A1 | 3/2000 |
| DE | 102008047233 A1 | 4/2010 |
| EP | 0298222 A2 | 1/1989 |
| EP | 0936884 A1 | 8/1999 |
| EP | 0936224 B1 | 7/2003 |
| GB | 340232 | 12/1930 |
| GB | 765811 | 1/1957 |
| GB | 870081 | 6/1961 |
| GB | 927542 | 5/1963 |
| GB | 1084061 | 9/1967 |
| GB | 1314897 | 4/1973 |
| GB | 2266100 A | 10/1993 |
| WO | WO9419448 A1 | 9/1994 |
| WO | WO9936469 A1 | 7/1999 |
| WO | WO0146357 A2 | 6/2001 |
| WO | WO0210330 A1 | 2/2002 |
| WO | WO0215849 | 2/2002 |
| WO | WO03105786 A2 | 12/2003 |
| WO | WO2004056890 A1 | 7/2004 |
| WO | WO2004069978 A1 | 8/2004 |
| WO | WO2006055505 A2 | 5/2006 |
| WO | WO2006055787 A1 | 5/2006 |
| WO | WO2006076065 A2 | 7/2006 |
| WO | WO2007012981 A2 | 2/2007 |
| WO | WO2007062833 | 6/2007 |
| WO | WO2008005693 | 1/2008 |
| WO | WO2008152543 | 12/2008 |
| WO | WO2009037060 | 3/2009 |
| WO | WO2009087525 | 7/2009 |
| WO | WO2010105922 | 9/2010 |
| WO | WO2011056904 | 5/2011 |

OTHER PUBLICATIONS

Yang et al., Adsorption—solution structure relationships of PET/POET polymeric surfactants in aqueous solutions, Polymer, 1996, vol. 37, pp. 4621-4627.

PCT International Search Report in PCT application PCT/EP2012/064897 dated Oct. 17, 2012 with Written Opinion.

PCT International Search Report in PCT application PCT/CN2011/001415 dated May 31, 2012 with Written Opinion.

PCT International Search Report in PCT application PCT/EP2012/064898 dated Oct. 16, 2012 with Written Opinion.

PCT International Search Report in PCT application PCT/CN2011/001413 dated May 31, 2012 with Written Opinion.

PCT International Search Report in PCT application PCT/CN2011/001414 dated Apr. 19, 2012 with Written Opinion.

PCT International Search Report in PCT application PCT/CN2011/001412 dated May 31, 2012 with Written Opinion.

PCT International Search Report in PCT application PCT/EP2011/064071 dated Nov. 7, 2011 with Written Opinion.

PCT International Search Report in PCT application PCT/CN2010/076087 dated May 26, 2011 with Written Opinion.

Co-pending Application: Applicant: Chen et al., Filed: Feb. 19, 2014.

Co-pending Application: Applicant: Chen et al., U.S. Appl. No. 14/164,886, filed Jan. 27, 2014.

Charles E. Carraher, Jr., General Property Performance-Strucutre Relationships, Polymer Chemistry, (2008) pp. 41-42.

Titus et al., Polysaccharides, Chemistry of Food Additives and Preservatives, (2012) p. 68.

* cited by examiner

BENEFIT AGENT DELIVERY PARTICLES COMPRISING DEXTRAN

TECHNICAL FIELD

The present invention relates to surface treatment compositions and, more specifically, to compositions comprising particles which comprise a benefit agent (preferentially perfume) and the deposition aid. The invention also relates to delivery of the benefit agent (preferably perfume) for example to fabric during laundering, or to human body substrate surfaces such as skin or more preferably hair.

BACKGROUND OF THE INVENTION

The present invention will be described with particular reference to perfume as the benefit agent although the technology is believed applicable to other benefit agents used in surface treatment processes.

In laundry applications deposition of a perfume is used, for example, during fabric treatment processes such as fabric washing and conditioning. Methods of deposition are diverse and include deposition during the wash or rinse stages of the laundry process or direct deposition before or after the wash, such as by spraying or rubbing or by use of impregnated sheets during tumble drying or water additives during steam ironing. The perfume is often incorporated into a carrier or delivery system. Carrier systems for perfumes are typically based on encapsulation or entrapment of the perfume within a matrix.

After deposition onto a surface, a problem exists in that longevity of adherence to that surface of the perfume, in a surfactant containing environment, is inherently poor. A perfume which has been deposited onto a fabric may be washed off again during a main wash, or the perfume may be leached from its carrier into the wash. Protection of the perfume is, therefore, required before and after it has been deposited onto a surface. Much the same problems are encountered with other benefit agents, which are, like perfume typically relatively expensive and present in laundry compositions at relatively low levels.

Similar problems occur in the fields of skin and hair treatment, where perfumes and/or other benefit agents are to be deposited on the skin or the hair.

WO 07/62833 relates to compositions which comprise core-shell encapsulated perfume particles decorated with a polysaccharide which is substantive to cellulose. Preferred polysaccharides disclosed therein are locust bean gum, tamarind xyloglucan, guar gum or mixtures thereof. Thus it is known to have particles comprising a benefit agent (perfume) which use cellulose-substantive polysaccharide as a delivery aid to assist the particles in binding to a specific substrate. The compositions may also comprise one or more enzymes. Suitable enzymes disclosed in the reference include, amongst others, those known as cellulase.

The term cellulase refers to a class of enzymes which show a range of possible reactions on a variety of substrates. One problem with cellulose-substantive polysaccharides is that they have a structure which is generally similar to cellulose, and as such, are subject to attack by "cellulase".

Similar benefit agent delivery aids have been suggested for polyester, based on phthalate containing polymers similar to so-called soil release polymers. These phthalate polymers are subject to problems of hydrolysis and are not substantive to cotton.

A number of documents disclose that cellulosic materials can also function as soil release polymers and anti-redeposition agents. The use of methyl and ethyl cellulose ethers in detergent compositions is disclosed in U.S. Pat. No. 2,373,863, Vitalis (1945). A great many cellulosics for use in detergents are disclosed in U.S. Pat. No. 2,994,665, Reich, et al. (1961); see also U.S. Pat. No. 3,523,088, Dean, et al. (1970). German Auslegeschrift No. 1,054,638, Van der Werth, Nov. 2, 1956, discloses C12 alkyl benzene sulfonates in combination with carboxylated cellulose derivatives. British Patent No. 1,084,061 discloses low amounts of cellulosics as stabilizers for liquid detergents. British Patent Nos. 927,542; 765,811; and 340,232 also teach cellulosics in detergents.

U.S. Pat. No. 4,174,305 discloses alkyl benzene sulfonate detergent compositions containing cellulose ether soil release agents. U.S. Pat. No. 4,732,639 discloses that some alkyl or alkyl/hydroxy-alkyl cellulose derivatives (with a molar degree of substitution of up to 3.0) are effective as soil release polymers and/or as anti-redeposition polymers. UK 1314897 discloses that hydroxy-propyl methyl cellulose for use as an anti-redeposition and soil release aid, but from that document (as observed in U.S. Pat. No. 6,191,093) it can be seen that performance is somewhat unsatisfactory on pure cotton articles. U.S. Pat. No. 6,200,351 discloses nonionic hydroxy-alkyl cellulose ethers suitable for use as soil release polymers in combination with polyester soil release polymers, which include in particular hydroxy-ethyl, hydroxy-propyl and/or hydroxy-butyl celluloses which may additionally carry alkyl ether groups, more particularly, methyl, ethyl and/or propyl groups.

A need exists for a deposition system which is effective both on cotton and polyester and is stable against hydrolysis and enzyme attack. There is also a need to find effective deposition aids for other substrates.

BRIEF DESCRIPTION OF THE INVENTION

We have now determined that particles comprising a benefit agent which use dextran as a delivery aid are effective on cotton and on polyester as well as on hair.

Accordingly, a first aspect of the present invention provides a benefit agent delivery particle having at the outer surface of the particle one or more delivery aids which are polysaccharides and which include dextran.

It is preferable that the delivery aid consists essentially of dextran.

Preferably the benefit agent delivery particle comprises a non-polysaccharide polymer, more preferably an aminoplast polymer. Typically, the non-polysaccharide polymer is cross linked in the form of relatively large water-insoluble macromolecules.

Preferably the benefit agent delivery particle comprises a perfume.

Highly preferred particles comprise a core which comprises the benefit agent and at least one shell which comprises the water insoluble non-polysaccharide polymer, with the dextran attached at the outer surface of the outermost shell.

Such particles have an inner region, typically forming a "core" which contains the benefit agent and a water-insoluble "shell" which protects the benefit agent and regulates the flow of benefit agent into and out of the core. The core may comprise a droplet of the benefit agent or may comprise a polymer matrix into which the benefit agent is adsorbed.

The particle can be a carrier which controls thermodynamic (rather than kinetic) partition of the benefit agent between the interior region and elsewhere. This is particularly advantageous where late-stage addition of perfume or other benefit agent is required as the particles and the benefit agent may therefore be dosed into the product separately. In the alternative, the shell is largely impermeable to the benefit agent and the benefit agent is released on breakage of the shell.

Preferably the benefit agent delivery particle comprises a core and at least one shell. In particularly preferred embodiments perfume is present in the core and the delivery aid is attached to the outside of the outermost shell. While it is preferred that the delivery aid is attached directly to the shell it may be attached via a linking species.

By attachment is meant that the delivery aid is not removed in water, thus the delivery aid is a permanent part of the encapsulate and not a water-soluble coating.

It is envisaged that a further benefit of the benefit agent delivery particles of the present invention is that they will also give some soil release benefits in laundry applications due to the enhanced affinity to cotton which the delivery aid gains by it's attachment to a particle.

A further aspect of the present invention provides a hair, skin or laundry treatment composition comprising:
a) a particle according to the first aspect of the invention, and,
b) at least one surfactant.

In a particularly preferred embodiment the invention provides a liquid treatment composition comprising at least one anionic or non-ionic surfactant.

Preferably, for hair and/or skin treatment compositions the surfactant comprises at least 3% wt on total composition of an alkyl ether sulphate.

Advantageously, the delivery aid is not susceptible to hydrolysis and is not attacked by the enzymes that are typically used in laundry compositions.

In a preferred embodiment the laundry treatment compositions of the invention comprise at least one enzyme with a polysaccharide substrate. Preferably this is selected from hemicellulase, cellulase (which is particularly preferred), polygalacturonase, xylanase, pectinase, mannanase (which is also particularly preferred), pectate lyase, ligninase, pullulanase, pentosanase, arabinosidase, hyaluronidase, chondroitinase, laccase, glycosylhydrolase, and amylases, or mixtures thereof. In another preferred embodiment the compositions of the invention contain polyesterase. Both polyesterase and the polysaccharide-substrate enzymes can be present. The stability of the delivery aid in the presence of these common enzymes, particularly cellulase, gives a significant advantage over the previously known deposition systems based on Locust Bean Gum.

In another preferred embodiment the compositions of the invention contain polyesterase. Both polyesterase and the polysaccharide-substrate enzymes can be present.

Further preferred compositions comprise an enzyme selected from cellulase, mannanase and mixtures thereof and polymeric core-shell particles comprising perfume, characterised in that, dextran is attached to the outside of the shell of the particles as a delivery aid.

A yet further aspect of the present invention subsists in a process for the production of benefit agent delivery particles, in which:
a) a core is encapsulated using emulsion polymerization to form core-shell particles, and,
b) a further polymer layer is formed on the outer surface of the core shell-particles in the presence of dextran,
wherein the benefit agent is either present in or as the core during step (a) of the process or adsorbed into the core in a subsequent step.

DETAILED DESCRIPTION OF THE INVENTION

In order that the present invention may be further understood it is described in further detail below with particular reference to preferred features. Where percentages are given they are, unless described otherwise percentages by weight. Similarly, all ratios are ratio's by weight unless otherwise specified.

Except in the operating and comparative examples, or where otherwise explicitly indicated, all numbers in this description indicating amounts or ratios of material or conditions of reaction, physical properties of materials and/or use are to be understood as modified by the word "about".

Delivery Aid

Dextran is an α-D-1,6-glucose-linked glucan with side-chains 1-3 linked to the backbone units of the dextran biopolymer. Typically the degree of branching is approximately 5%. The branches are mostly 1-2 glucose units long. It is surprising that an alpha 1-6 polysaccharide should show any affinity for both cellulose and polyester.

Preferably the dextran has a molecular weigh above 5 kD, more preferably above 10 kD and most preferably above 20 kD.

Benefit Agents

Benefit agents provide a range of benefits to, as the case may be, skin, fabrics or hair Various benefit agents can be incorporated into the particles. Where the end use of the particles is in connection with the preferred surfactant-containing formulations, any compatible benefit agent which can provide a benefit to a substrate which is treated with a preferably surfactant-containing composition can be used. Advantages of the particles of the invention in the presence of surfactant are a good retention of the benefit agent on storage of a formulation and controllable release of the benefit agent during and after product usage.

Benefit agents provide a range of benefits to cloth. These include benefits of softening, conditioning, lubricating, crease reducing, ease of ironing, moisturising, colour preserving and/or anti-pilling, quick drying, UV protecting, shape retaining, soil releasing, texturising, insect repelling, fungicidal, dyeing and/or fluorescent benefit to the fabric.

A highly preferred benefit is the delivery of fragrance (whether free and/or encapsulated), or pro-fragrance.

Preferred benefit agents are perfumes (whether free and/or encapsulated), pro-fragrance, clays, enzymes, antifoams, fluorescers, bleaching agents and precursors thereof (including photo-bleach), shading dyes and/or pigments, fabric conditioning agents (for example cationic surfactants including water-insoluble quaternary ammonium materials and/or silicones), lubricants (e.g. sugar polyesters), photo-protective agents (including sunscreens), antioxidants, reducing agents, sequestrants, colour care additives (including dye fixing agents), unsaturated oil, emollients, insect repellents and/or pheromones, drape modifiers (e.g. polymer latex particles such as PVAc) and anti-microbial and microbe control agents. Mixtures of two or more of these may be employed. Particular benefit agents are described in further detail below.

Other preferred benefit agents are flavours and fragrances, profragrance, clays, enzymes, antifoams, fluorescers, bleaching agents and precursors thereof (including photo-bleach), dyes and/or pigments, conditioning agents (for example cationic surfactants including water-insoluble quaternary ammonium materials, fatty alcohols and/or silicones), lubricants (e.g. sugar polyesters), colour and photo-protective agents (including sunscreens), antioxidants, ceramides, reducing agents, sequesterants, colour care additives (including dye fixing agents), unsaturated oil, emollients, moisturisers, insect repellents and/or pheromones, drape modifiers (e.g. polymer latex particles such as PVAc) and anti-microbial and microbe control agents. Mixtures of two or more of these may be employed. Particular benefit agents are described in further detail below.

For skin compositions the preferred benefit agents include one or more of fragrances, moisturisers, sunscreens, skin lightening agents, antimicrobials, oils and insect repellents. For hair compositions the list of preferred benefit agents is the same with the addition of colour protection agents and dyes.

Preferred antimicrobials include Triclosan™, climbazole, octapyrox, ketoconizole, zinc pyrithione, and quaternary ammonium compounds.

Antidandruff agents are benefit agents suitable for use in hair treatment compositions that are active against dandruff and are typically antimicrobial agents and preferably antifungal agents. Antifungal agents typically display a minimum inhibitory concentration of about 50 mg/ml or less against *Malassezia* spp.

Suitable antidandruff benefit agents include compounds selected from ketoconazole, climbazole, octopirox, metal pyrithione salts, and mixtures thereof. The preferred azole based antifungal agents are ketoconazole and climbazole.

Preferred metal pyrithione salts are zinc, copper, silver and zirconium pyrithione. The most preferred is zinc pyrithione.

Preferably, the antidandruff active is present at from 0.01 to 5% wt. of the composition, more preferably from 0.1 to 2.5% wt. of the composition.

Preferred sunscreens and/or skin lightening agents are vitamin B3 compounds. Suitable vitamin B3 compounds are selected from niacin, niacinamide, nicotinyl alcohol, or derivatives or salts thereof. Other vitamins which act as skin lightening agents can be advantageously included in the skin lightening composition to provide for additional skin lightening effects. These include vitamin B6, vitamin C, vitamin A or their precursors. Mixtures of the vitamins can also be employed in the composition of the invention. An especially preferred additional vitamin is vitamin B6. Other non-limiting examples of skin lightening agents useful herein include adapalene, aloe extract, ammonium lactate, arbutin, azelaic acid, butyl hydroxy anisole, butyl hydroxy toluene, citrate esters, deoxyarbutin, 1,3 diphenyl propane derivatives, 2, 5 di hydroxylbenzoic acid and its derivatives, 2-(4-acetoxyphenyl)-1,3 dithane, 2-(4-Hydroxylphenyl)-1,3 dithane, ellagic acid, gluco pyranosyl-1-ascorbate, gluconic acid, glycolic acid, green tea extract, 4-Hydroxy-5-methyl-3[2H]-furanone, hydroquinone, 4 hydroxyanisole and its derivatives, 4-hydroxy benzoic acid derivatives, hydroxycaprylic acid, inositol ascorbate, kojic acid, lactic acid, lemon extract, linoleic acid, magnesium ascorbyl phosphate, 5-octanoyl salicylic acid, 2,4 resorcinol derivatives, 3,5 resorcinol derivatives, salicylic acid, 3,4,5 trihydroxybenzyl derivatives, and mixtures thereof. Preferred sunscreens useful in the present invention are 2-ethylhexyl-p-methoxycinnamate, butyl methoxy dibenzoylmethane, 2-hydroxy-4-methoxybenzophenone, octyl dimethyl-p-aminobenzoic acid and mixtures thereof. Particularly preferred sunscreen is chosen from 2-ethyl hexyl-p-methoxycinnamate, 4,-t-butyl-4'-methoxydibenzoyl-methane or mixtures thereof. Other conventional sunscreen agents that are suitable for use in the skin lightening composition of the invention include 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexyl-salicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonic benzoxazoic acid and mixtures of these compounds.

Preferred anti-oxidants include vitamin E, retinol, antioxiants based on hydroxytoluene such as Irganox™ or commercially available antioxidants such as the Trollox™ series.

Benefit Agent Association and Carriers

The delivery aid is attached to a particle which either comprises the benefit agent per-se or which is itself a carrier for the benefit agent. An example of such would be a perfume antidandruff, insect repellent or other benefit agent carrying particle with the delivery aid attached to the surface of the particle.

While it is preferred to use polymer particles, preferably core-shell encapsulates, many other types of particle can be envisaged as the benefit agent carrier. Perfumes have been adsorbed onto a clay or zeolite material that is then admixed into particulate detergent compositions: U.S. Pat. No. 4,539, 135 discloses particulate laundry compounds comprising a clay or zeolite material carrying perfume. Combinations of perfumes generally with larger pore size zeolites such as zeolite X and Y are also taught in the art. East German Patent Publication No. 248,508, relates to perfume dispensers containing a faujasite-type zeolite (e.g., zeolite X and Y) loaded with perfume. Also, East German Patent Publication No. 137,599, published Sep. 12, 1979 teaches compositions for use in powdered washing agents to provide thermo-regulated release of perfume. Zeolites A, X and Y are taught for use in these compositions. Other perfume delivery systems are taught by WO 97/34982 and WO 98/41607, published by The Procter & Gamble. WO 97/34982 discloses particles comprising perfume loaded zeolite and a release barrier, which is an agent derived from a wax and having a size (i.e., a cross-sectional area) larger than the size of the pore openings of the zeolite carrier. WO 98/41607 discloses glassy particles comprising agents useful for laundry or cleaning compositions and a glass derived from one or more of at least partially-water-soluble hydroxylic compounds.

Silicas, amorphous silicates, crystalline nonlayer silicates, layer silicates, calcium carbonates, calcium/sodium carbonate double salts, sodium carbonates, sodalites, alkali metal phosphates, pectin, chitin microbeads, carboxyalkylcelluloses, gums, resins, gelatin, gum arabic, porous starches, modified starches, carboxyalkyl starches, cyclodextrins, maltodextrins, synthetic polymers such as polyvinyl pyrrolidone (PVP), polyvinyl alcohol (PVA), cellulose ethers, polystyrene, polyacrylates, polymethacrylates, polyolefins, aminoplast polymers, crosslinkers and mixtures thereof can all provide a basis for perfume particles.

Polymer particles are however preferred, especially polymer particles which comprise an aminoplast polymer.

The benefit agent carrying particles are typically of a size between 100 nanometers and 50 microns. Particles larger than this are entering the visible range.

The preferred particle size range is either in the sub-micron range or the micron range.

Suitable particles in the sub-micron range include nanoparticles, latexes, and mini-emulsion products with a typical size range of 100-600 nanometers.

Suitable particles in the micron range include known types of melamine/urea-formaldehyde encapsulates, silica, clays starch and zeolite particles and coacervates with a typical size range of 1-50 microns, preferably 5-30 microns.

In one preferred aspect of the invention the dextran, as deposition aid, is attached to at least partially pre-formed particles.

The delivery aid is bound to the particle by means of a covalent bond, entanglement or strong adsorption, preferably by a covalent bond or entanglement and most preferably by means of a covalent bond. By entanglement as used herein is meant that the delivery aid is adsorbed onto the particle as the polymerisation proceeds and the particle grows in size. It is believed that under such circumstances part of the adsorbed delivery aid becomes buried within the interior of the particle. Hence at the end of the polymerisation, part of the delivery aid is entrapped and bound in the polymer matrix of the particle, whilst the remainder is free to extend into the aqueous phase.

The delivery is preferably mainly attached to the particle surface and is not, to any significant extent, distributed throughout the internal bulk of the particle. Thus the particle which is produced when using a delivery aid according to the preferred process of the invention can be thought of as a "hairy particle". As noted above, it is important that the dextran is not removed by water as it cannot then function effectively as a delivery aid. Thus, for example spray-drier coating of dextran onto particles would not result in dextran being an effective delivery aid as the dextran would be removed from the particles on exposure to water.

The polymer carrier particles of the invention can comprise a wide selection of monomer units. By "monomer units" as used herein is meant the monomer units of the polymer chain, thus references to "a polymer particle comprising insoluble monomer units" as used herein means that the polymer particles is derived from insoluble monomers, and so forth.

As noted above, the monomer units are preferably derived from monomers which are suitable for either step growth polymerisation or addition/free radical polymerisation. As noted above aminoplast (for example melamine/formaldehyde or urea/formaldehyde) core/shell particles with benefit agent present in the core and the chitosan salt attached to the outer surface of the shell are particularly preferred Where the particle itself is not the benefit agent, the benefit agent is typically present in an amount of from 10-85% by total weight of the carrier particle, preferably from 20 to 75% by total weight of the particle.

While it is essential for the present invention that the delivery aid comprises a dextran, additional delivery aids may be present at the surface of the particle. These can advantageously be selected from cellulose derivatives and polyesters, so give better substantivity to a plurality of substrates. Particularly preferred polysaccharide additional deposition aids include chitosan, hydroxy-propyl methyl cellulose, hydroxy-ethyl methyl cellulose, hydroxy-propyl guar, hydroxy-ethyl ethyl cellulose, methyl cellulose, locust bean gum, xyloglucan, guar gum. Particularly preferred polyester additional deposition aids include polymers having one or more non-ionic hydrophilic components comprising oxyethylene, polyoxyethylene, oxypropylene or polyoxypropylene segments, and, one or more hydrophobic components comprising terephthalate segments.

Volatile Benefit Agents including Perfume as the Benefit Agent

Perfume is one example of a volatile benefit agent. Typical volatile benefit agents have a molecular weight of from 50 to 500. The perfume suitably has a molecular weight of from 50 to 500. Where pro-fragrances are used the molecular weight will generally be higher.

Useful components of the perfume include materials of both natural and synthetic origin. They include single compounds and mixtures. Specific examples of such components may be found in the current literature, e.g., in Fenaroli's Handbook of Flavour Ingredients, 1975, CRC Press; Synthetic Food Adjuncts, 1947 by M. B. Jacobs, edited by Van Nostrand; or Perfume and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally perfumed or flavoured, or of modifying the odour and/or taste of said consumer product.

By perfume in this context is not only meant a fully formulated product fragrance, but also selected components of that fragrance, particularly those which are prone to loss, such as the so-called 'top notes'. The perfume component could also be in the form of a pro-fragrance. WO 2002/038120 (P&G), for example, relates to photo-labile pro-fragrance conjugates which upon exposure to electromagnetic radiation are capable of releasing a fragrant species.

Top notes are defined by Poucher (Journal of the Society of Cosmetic Chemists 6(2):80 [1955]). Examples of well known top-notes include citrus oils, linalool, linalyl acetate, lavender, dihydromyrcenol, rose oxide and cis-3-hexanol. Top notes typically comprise 15-25% wt of a perfume composition and in those embodiments of the invention which contain an increased level of top-notes it is envisaged at that least 20% wt would be present within the encapsulate.

Typical perfume components which it is advantageous to encapsulate, include those with a relatively low boiling point, preferably those with a boiling point of less than 300, preferably 100-250 Celsius.

It is also advantageous to encapsulate perfume components which have a low LogP (ie. those which will be partitioned into water), preferably with a LogP of less than 3.0. These materials, of relatively low boiling point and relatively low LogP have been called the "delayed blooming" perfume ingredients and include the following materials:

Allyl Caproate, Amyl Acetate, Amyl Propionate, Anisic Aldehyde, Anisole, Benzaldehyde, Benzyl Acetate, Benzyl Acetone, Benzyl Alcohol, Benzyl Formate, Benzyl Iso Valerate, Benzyl Propionate, Beta Gamma Hexenol, Camphor Gum, Laevo-Carvone, d-Carvone, Cinnamic Alcohol, Cinamyl Formate, Cis-Jasmone, cis-3-Hexenyl Acetate, Cuminic Alcohol, Cyclal C, Dimethyl Benzyl Carbinol, Dimethyl Benzyl Carbinol Acetate, Ethyl Acetate, Ethyl Aceto Acetate, Ethyl Amyl Ketone, Ethyl Benzoate, Ethyl Butyrate, Ethyl Hexyl Ketone, Ethyl Phenyl Acetate, Eucalyptol, Eugenol, Fenchyl Acetate, Flor Acetate (tricyclo Decenyl Acetate), Frutene (tricycico Decenyl Propionate), Geraniol, Hexenol, Hexenyl Acetate, Hexyl Acetate, Hexyl Formate, Hydratropic Alcohol, Hydroxycitronellal, Indone, Isoamyl Alcohol, Iso Menthone, Isopulegyl Acetate, Isoquinolone, Ligustral, Linalool, Linalool Oxide, Linalyl Formate, Menthone, Menthyl Acetphenone, Methyl Amyl Ketone, Methyl Anthranilate, Methyl Benzoate, Methyl Benzyl Acetate, Methyl Eugenol, Methyl Heptenone, Methyl Heptine Carbonate, Methyl Heptyl Ketone, Methyl Hexyl Ketone, Methyl Phenyl Carbinyl Acetate, Methyl Salicylate, Methyl-N-Methyl Anthranilate, Nerol, Octalactone, Octyl Alcohol, p-Cresol, p-Cresol Methyl Ether, p-Methoxy Acetophenone, p-Methyl Acetophenone, Phenoxy Ethanol, Phenyl Acetaldehyde, Phenyl Ethyl Acetate, Phenyl Ethyl Alcohol, Phenyl Ethyl Dimethyl Carbinol, Prenyl Acetate, Propyl Bornate, Pulegone, Rose Oxide, Safrole, 4-Terpinenol, Alpha-Terpinenol, and/or Viridine It is commonplace for a plurality of perfume components to be present in a formulation. In the encapsulates of the present invention it is envisaged that there will be four or more, preferably five or more, more preferably six or more or even seven or more different perfume components from the list given of delayed blooming perfumes given above present in the encapsulated perfume.

Part or all of the perfume may be in the form of a pro-fragrance. For the purposes of the present invention a pro-fragrance is any material which comprises a fragrance precursor that can be converted into a fragrance. The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols. In their natural state, plant lipids comprise antioxidants to prevent their oxidation. While these may be at least in part removed during the isolation of oils from plants some antioxidants may remain. These antioxidants can be pro-fragrances. In particular, the carotenoids and related compounds including vitamin A, retinol, retinal, retinoic acid and provitamin A are capable of being converted into fragrant species including the ionones, damascones and damscenones. Preferred pro-fragrance food lipids include olive oil, palm oil, canola oil, squalene, sunflower seed oil, wheat germ oil, almond oil, coconut oil, grape seed oil, rapeseed oil, castor oil, corn oil, cottonseed oil, safflower oil, groundnut oil, poppy seed oil, palm kernel oil, rice bran oil, sesame oil, soybean oil, pumpkin seed oil, jojoba oil and mustard seed oil.

Suitable pro-fragrances are those that generate perfume components which are aldehydes. Aldehydes useful in perfumery include but are not limited to phenylacetaldehyde, p-methyl phenylacetaldehyde, p-isopropyl phenylacetaldehyde, methylnonyl acetaldehyde, phenylpropanal, 3-(4-t-butylphenyl)-2-methyl propanal, 3-(4-t-butylphenyl)-propanal, 3-(4-methoxyphenyl)-2-methylpropanal, 3-(4-isopropylphenyl)-2-methylpropanal, 3-(3,4-methylenedioxyphenyl)-2-methyl propanal, 3-(4-ethylphenyl)-2,2-dimethylpropanal, phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal, 2,4-heptadienal, octanal, 2-octenal, 3,7-dimethyloctanal, 3,7-dimethyl-2,6-octadien-1-al, 3,7-dimethyl-1,6-octadien-3-al, 3,7-dimethyl-6-octenal, 3,7-dimethyl-7-hydroxyoctan-1-al, nonanal, 6-nonenal, 2,4-nonadienal, 2,6-nonadienal, decanal, 2-methyl decanal, 4-decenal, 9-decenal, 2,4-decadienal, undecanal, 2-methyl-decanal, 2-methylundecanal, 2,6,10-trimethyl-9-undecenal, undec-10-enyl aldehyde, undec-8-enanal, dodecanal, tridecanal, tetradecanal, anisaldehyde, bourgenonal, cinnamic aldehyde, a-amylcinnam-aldehyde, a-hexyl cinnamaldehyde, methoxy-cinnamaldehyde, citronellal, hydroxy-citronellal, isocyclocitral, citronellyl oxyacet-aldehyde, cortexaldehyde, cumminic aldehyde, cyclamen aldehyde, florhydral, heliotropin, hydrotropic aldehyde, lilial, vanillin, ethyl vanillin, benzaldehyde, p-methyl benzaldehyde, 3,4-dimethoxy benzaldehyde, 3- and 4-(4-hydroxy-4-methyl-pentyl)-3-cyclohexene-1-carboxaldehyde, 2,4-dimethyl-3-cyclohexene-1-carboxaldehyde, 1-methyl-3-(4-methylpentyl)-3-cyclohexen-carboxaldehyde, p-methylphenoxyacetaldehyde, and mixtures thereof.

Another group of perfumes with which the present invention can be applied are the so-called 'aromatherapy' materials. These include many components also used in perfumery, including components of essential oils such as Clary Sage, Eucalyptus, Geranium, Lavender, Mace Extract, Neroli, Nutmeg, Spearmint, Sweet Violet Leaf and Valerian. By means of the present invention these materials can be transferred to textile articles that will be worn or otherwise come into contact with the human body (such as handkerchiefs and bed-linen) or deposited directly on human skin or hair.

The volatile benefit agents also include insect repellent materials (where insect should be read broadly to include other pests which are arthropods but not strictly hexapods—for example ticks). Many of these materials overlap with the class of perfume components and some are odourless to humans or have a non-perfume odour. Commonly used repellents include: DEET (N,N-diethyl-m-toluamide), essential oil of the lemon eucalyptus (Corymbia citriodora) and its active compound p-menthane-3,8-diol (PMD), Icaridin, also known as Picaridin, D-Limonene, Bayrepel, and KBR 3023, Nepetalactone, also known as "catnip oil", Citronella oil, Permethrin, Neem oil and Bog Myrtle. Known insect repellents derived from natural sources include: *Achillea alpina*, alpha-terpinene, Basil oil (*Ocimum basilicum*), *Callicarpa americana* (Beautyberry), Camphor, Carvacrol, Castor oil (*Ricinus communis*), Catnip oil (*Nepeta* species), Cedar oil (*Cedrus atlantica*), Celery extract (*Apium graveolens*), Cinnamon (*Cinnamomum Zeylanicum*, leaf oil), Citronella oil (*Cymbopogon fleusus*), Clove oil (*Eugenic caryophyllata*), Eucalyptus oil (70%+eucalyptol, also known as cineol), Fennel oil (*Foeniculum vulgare*), Garlic Oil (*Allium sativum*), Geranium oil (also known as *Pelargonium graveolens*), Lavender oil (*Lavandula officinalis*), Lemon eucalyptus (*Corymbia citriodora*) essential oil and its active ingredient p-menthane-3,8-diol (PMD), Lemongrass oil (*Cymbopogon flexuosus*), Marigolds (*Tagetes* species), Marjoram (*Tetranychus urticae* and *Eutetranychus orientalis*), Neem oil (*Azadirachta indica*), Oleic acid, Peppermint (*Mentha×piperita*), Pennyroyal (*Mentha pulegium*), Pyrethrum (from *Chrysanthemum* species, particularly *C. cinerariifolium* and *C. coccineum*), Rosemary oil (*Rosmarinus officinalis*), Spanish Flag *Lantana camara* (*Helopeltis theivora*), *Solanum villosum* berry juice, Tea tree oil (*Melaleuca alternifolia*) and Thyme (*Thymus* species) and mixtures thereof.

The perfume may be encapsulated alone or co-encapsulated with carrier materials, further deposition aids and/or fixatives. Preferred materials to be co-encapsulated in carrier particles with the perfume include waxes, paraffins, stabilizers and fixatives.

An optional yet preferred component of carrier particles is a formaldehyde scavenger. This is particularly advantageous in carrier particles which may comprise formaldehyde as a consequence of their manufacturing process or components. Formaldehyde scavenger is chosen from: sodium bisulfite, urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly (vinyl alcohol), poly(vinyl amine), hexane diol, ethylenediamine-N,N'-bisacetoacetamide, N-(2-ethylhexyl)acetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, benzylamine, hydroxycitronellol, cyclohexanone, 2-butanone, pentane dione, dehydroacetic acid, chitosan, or a mixture thereof. Preferred formaldehyde scavengers are sodium bisulfite, ethyl acetoacetate, acetoacetamide, ethylenediamine-N,N'-bisacetoacetamide, ascorbic acid, 2,2-dimethyl-1,3-dioxan-4,6-dione, helional, triplal, lilial and mixtures thereof.

Enzymes

In laundry applications t is preferred that the compositions according to the invention comprise one or more enzymes. When present in a cleaning composition, the aforementioned enzymes may be present at levels from about 0.00001 wt. % to about 2 wt. %, from about 0.0001 wt. % to about 1 wt. % or even from about 0.001 wt. % to about 0.5 wt. % enzyme protein by weight of the composition.

Process Details

In the highly preferred embodiments in which the particles have a distinct core and shell, a typical process for the production of the particles will involve at least one emulsion polymerisation step.

For those embodiments where the core essentially comprises a hydrophobic benefit agent, the emulsion polymerisation can take the form of dispersing the benefit agent in an aqueous system with appropriate materials to form the required polymer shell present either in the benefit agent or the aqueous system.

Polymerisation then proceeds at the surface of the dispersed droplets of benefit agent (or benefit agent plus fixative or carrier) to form a shell around a core comprising the benefit agent. Such methods are well known, for example to produce aminoplast perfume encapsulates.

In those embodiments of the invention which have a polymer-containing core polymerisation may occur in at least two phases, in which the shell and the core are formed sequentially. The shell can be polymerised after the core or the order of polymerisation can be reversed.

Core First: In this approach the core is formed first and the shell is deposited onto the core.

Core Second: In this approach polymerisation occurs in at least two phases. In an earlier of these phases a shell is formed by a step-growth polymerisation. This shell encloses and contains the reagents for the chain-growth reaction which occurs in a later phase. Temporal separation of these phases is accomplished by control of the reagents present and the reaction conditions. Typically, at least one of the components of the shell-forming reaction is withheld from the initial reaction mixture and added gradually to control the progress of the reaction in the shell-forming phase. Advantageously, the first phase of the reaction is performed under conditions in which the chain-growth reaction is inhibited. These conditions include a sufficiently low temperature (for a thermally activated reaction) or conditions of sufficiently low light (for a photo-activated reaction). Once the shell-forming reaction has proceeded sufficiently, the conditions are modified (for example, by raising the temperature or exposing the reaction mixture to light) to cause the reaction to form the inner region to start. A preferred method is one in which an emulsion is formed comprising the chain-growth polymer components in a non-aqueous dispersed phase and the step-growth polymer components are at the interface between the dispersed phase and the continuous aqueous phase. Typically the aqueous phase comprises an emulsifying agent, and one of the co-monomers for the step-growth polymer. Depending on the polymer chemistry chosen it may also contain any diol, alcohol or amine cross-linking agent. The disperse phase comprises the chain-growth monomer, the initiator, any isocyanate or vinyl cross-linking agents, the other co-monomer for the step growth polymer and any optional benefit agent.

The benefit agent may be present in the reaction mixture, at a level to give the benefit agent levels in the resulting particles at the levels disclosed above, although it is also possible to form "empty" particles and subsequently expose them to a benefit agent which can be adsorbed into the core of the particle.

Surface modification materials are generally added to the aqueous phase towards the end of the process, where, for example, further monomer(s) can be added to form further shell material and bind additional materials to the outside of the particle.

For simple core-shell particles, the core excluding benefit agent is preferably less than or equal to 80% wt of mass, and the shell generally 20% wt or greater of the mass of the particle.

In a preferred embodiment the emulsion polymerisation step is a so-called "mini-emulsion" polymerisation, performed with a dispersed phase droplet size of below one micron. Sufficiently fine emulsions can be obtained by a range of methods, including sonication, and/or via high shear dynamic mixers or static mixers. Mini-emulsion products have excellent suspending properties.

Emulsifying Agents

Many emulsifying agents are known for use in emulsion polymerisation. Suitable emulsifying agents for use in the polymerisation process may comprise, but are not limited to, non-ionic surfactants such as polyvinylpyrrolidone (PVP), polyethylene glycol sorbitan monolaurate (Tween 20), polyethylene glycol sorbitan monopalmitate (tween 40), polyethylene glycol sorbitan monooleate (Tween 80), polyvinyl alcohol (PVA), and poly(ethoxy)nonyl phenol, ethylene maleic anhydride (EMA) copolymer, Easy-Sperse™ (from ISP Technologies Inc.), ionic surfactants such as partially neutralized salts of polyacrylic acids such as sodium or potassium polyacrylate or sodium or potassium polymethacrylate. Brij™-35, Hypermer™ A 60, or sodium lignosulphate, and mixtures thereof.

Emulsifiers may also include, but are not limited to, acrylic acid-alkyl acrylate copolymer, poly(acrylic acid), polyoxyalkylene sorbitan fatty esters, polyalkylene co-carboxy anhydrides, polyalkylene co-maleic anhydrides, poly(methyl vinyl ether-co-maleic anhydride), poly(propylene-co-maleic anhydride), poly(butadiene co-maleic anhydride), and poly(vinyl acetate-co-maleic anhydride), polyvinyl alcohols, polyalkylene glycols, polyoxyalkylene glycols, and mixtures thereof.

Preferred emulsifying agents are fatty alcohol exthoylates (particularly of the Brij™ class), salts of ether sulphates (including SLES), alkyl and alkaryl sulphonates and sulphates (including LAS and SDS) and cationic quaternary salts (including CTAC and CTAB).

The nature of the emulsifying agent can be selected to ensure that the finished particle is compatible with the environment in which it will be used.

In particular, cores which are formed in the presence of anionic surfactant systems (for example SLES 1-4 EO, preferably 1-3 EO and the others mentioned above) are compatible with products in which the environment comprises an anionic surfactant, such as, for example body-wash products and shampoos.

Cores which are formed in the presence of cationic surfactant (for example a cationic quaternary salt as mentioned above and in particular one of the alkyl trimethyl ammonium halides) are compatible with products in which the environment comprises a cationic surfactant, for example a hair conditioner.

It is particularly preferred that the emulsifying agent further comprises a nonionic surfactant. This is believed to produce a particle which deposits better on skin or hair than one produced soley with a charged surfactant emulsifier. It is also preferred that the non-ionic surfactant is hydrophilic, so as to promote the formation of a stable mini-emulsion. The alcohol ethoxylates with more than ten moles of ethoxylation, for example Synperonic A20 (C1320EO), yield good results.

DLS data for samples shows that as the level of surfactant increases the particle size becomes smaller, which is also advantageous.

Preferably, the ratio of non-ionic to anionic emulsifier should be greater than 1:1 (i.e. non-ionic is present in excess) and the total surfactant level should be >3% wt of the polymerisation mixture.

Co-surfactant:

Typically a co-surfactant will be present in the dispersed phase during polymerisation and some of this will remain in the resulting particle. Suitable co-surfactants for use in the present invention include hexadecane, cetyl alcohol, lauroyl peroxide, n-dodecyl mercaptan, dodecyl methacrylate, stearyl methacrylate, polystyrene, polydecene, mineral oils, isopropyl myristate $C_{13}$-$C_{15}$ alkyl benzoate and polymethyl methacrylate.

The preferred cosurfactants comprise hexadecane, polydecene and isopropyl myristate.

As a wt % of oil phase as a total, the co-surfactant is typically 0-20%, preferably 1-15%, more pref 2-12.5%.

Catalyst

Depending on the reactants present, optional catalyst may be present in the dispersed phase of the emulsion. For example in isocyanate/diol reactions a catalyst can advantageously minimises the hydrolysis of isocyanate to primary amine, which can react with further isocyanate to form polyurea. This unwanted reaction can result in an excess of diol being left at the end of the process which can potentially lead to the formation of malodour and interfere with cross-linking reactions.

Suitable catalysts may comprise amino or organo-metalic compounds such as N,N'-dimethylaminoethanol, N,N'-dimethylcyclohexylamine, bis-(2-dimethylaminoethyl)ether, N,N'-dimethylacetylamine, diaminobicyclooctane, stannous octoate and dibutyl tin dilaurate, 1,3-bis(dimethylamino) butane, pentamethyldiethylenetriamine and mixtures thereof.

When required, the level of catalyst is typically 0.1-2(Yowith respect to chain-growth monomer.

Deposition Aid Attachment

As noted above, polymerisation may occur in at least two phases. In one method during the earlier phase the shell is formed by a reaction which, in preferred embodiments occurs at less than about 60 Celsius, typically 15-55 Celsius. In the later phase the core is polymerised at a preferred temperature of more than about 70 Celsius, typically 70-95 Celsius. Both reactions are allowed to proceed for sufficiently long for polymerisation to be essentially complete, 1-3 hours being typical for each stage.

Deposition aid is typically added at or towards the end of shell formation when for example, further shell forming material (for example further isocyanate and co-momomer) are also added to bind the deposition aid to the outer surface of the particle by the formation of further shell material which entraps a portion of the deposition aid and leads to a "hairy" particle in which the "hair" comprises the deposition aid. In the alternative the particles can be essentially fully formed and the deposition aid attached by means of a chemical linkage.

In addition to the chitosan salts other deposition aid may be present. These are preferably nonionic materials and suitable deposition aids include Preferred Formulations:

In one embodiment of the invention the core of the particle comprises a rubbery polymeric material, i.e. one which has a Tg such that it is rubbery under conditions of storage. Suitable materials for the formation of cores with this property are the C2-C30, preferably C3-C18, more preferably C3-C12 acylates or methacrylates, with the butyl and methyl derivatives being particularly preferred. The core is intended to be a good solvent for the benefit agent.

Preferably the shell of the particle is a glassy material, i.e. one which has a Tg such that it is glassy under the conditions of storage. Suitable materials for the formation of shells with this property include the methyl methacrylates. The shell is intended to be a kinetic barrier for the benefit agent as well as maintaining capsule integrity. Typically the shell is 10-100 nm thick, preferably 20-40 nm.

The particles are typically included in compositions at levels of from 0.001% to 10%, preferably from 0.005% to 5%, most preferably from 0.01% to 3% by weight of the total composition.

Laundry Treatment Compositions

The delivery aid linked particles of the invention may be incorporated into laundry compositions. This may be done by mixing a slurry/dispersion product with some or all of the other components of the composition, for powders preferably by spraying onto the components. Advantageously, the slurry/dispersion need not be dried extensively (if at all) and this reduces benefit agent losses.

The active ingredient in the compositions for these laundry compositions is preferably a surface active agent or a fabric conditioning agent. More than one active ingredient may be included. For some applications a mixture of active ingredients may be used.

The compositions of the invention may be in any physical form e.g. a solid such as a powder or granules, a tablet, a solid bar, a paste, gel or liquid, especially, an aqueous based liquid. In particular the compositions may be used in laundry compositions, especially in liquid, powder or tablet laundry composition. Liquids are particularly preferred as the problems of hydrolysis and enzyme attack on the deposition aid are more marked in liquid compositions.

The laundry compositions, especially main wash (fabric washing) compositions or rinse-added softening compositions. The main wash compositions may include a fabric softening agent and the rinse-added fabric softening compositions may include surface-active compounds, particularly non-ionic surface-active compounds.

It is preferred that laundry compositions according to the invention comprise one or more enzymes. When present in a composition, the aforementioned enzymes may be present at levels from about 0.00001 wt. % to about 2 wt. %, from about 0.0001 wt. % to about 1 wt. % or even from about 0.001 wt. % to about 0.5 wt. % enzyme protein by weight of the composition.

A particularly preferred embodiment of the invention provides a laundry treatment composition comprising:
a) a benefit agent delivery particle having at the outer surface of the particle one or more delivery aids which include dextran, preferably wherein the dextran has a molecular weight above 5 kD, preferably above 20 kD, optionally wherein the particle further comprises a non-polysaccharide polymer (preferably an aminoplast polymer), optionally wherein the benefit agent comprises a perfume,
b) at least one anionic or non-ionic surfactant, and,
c) an enzyme selected from cellulase, mannanase and mixtures thereof.

Hair Treatment Compositions:

It is especially preferred that compositions of the present invention are hair treatment compositions and in particular are either hair shampoo compositions and/or hair conditioning compositions. As noted above the preferred benefit agents for delivery are one or more of fragrances, moisturisers, sunscreens, skin lightening agents, antimicrobials (especially anti-dandruff agents), oils, insect repellents, colour protection agents and dyes.

While the surfactants suitable for use in hair treatment compositions are described in further detail below, a particularly preferred hair treatment (shampoo) composition comprises a solution of 3-18% wt alkyl ether sulphate, 1-4% of a zwitterionic or amphoteric surfactant and 0.1-5% inorganic salt.

A particularly preferred embodiment of the invention provides a hair treatment composition comprising:
a) a benefit agent delivery particle having at the outer surface of the particle one or more delivery aids which include dextran, preferably wherein the dextran has a molecular weight above 5 kD, preferably above 20 kD, optionally wherein the particle further comprises a non-polysaccharide polymer (preferably an aminoplast polymer), optionally wherein the benefit agent comprises a perfume,
b) at least one anionic or non-ionic surfactant.

Hair conditioning compositions are especially preferred as the compositions of the invention give especially good deposition of the benefit agent containing particles on the distal region of the hair, whereas comparable compositions without the deposition aid give poor deposition in that region.

Use in Products

The end-product compositions of the invention may be in any physical form e.g., a solid bar, a paste, gel or liquid, or especially, an aqueous-based liquid.

The particles are typically included in said compositions at levels of from 0.001% to 10%, preferably from 0.005% to 7.55%, most preferably from 0.01% to 5% by weight of the total composition.

Depending on the end-use compositions according to the present invention will typically contain one or more of surfactants (which may be anionic, cationic, non-ionic, zwitterionic and ampphoteric), surfactant and/or non-surfactant conditioning agents, fatty alcohols, suspending agents and thickeners, polymers, silicones and shading agents.

Surfactants

The particles of the invention may be advantageously incorporated into surfactant-containing compositions, especially for use in the treatment of hair or laundry.

Formulated compositions comprising the particles of the invention may contain a surface-active compound (surfactant) which may be chosen from soap and non soap anionic, cationic, non-ionic, amphoteric and zwitterionic surface active compounds and mixtures thereof. Many suitable surface active compounds are available and are fully described in the literature, for example, in "Surface-Active Agents and Detergents", Volumes I and II, by Schwartz, Perry and Berch. The preferred surface-active compounds that can be used are soaps and synthetic non soap anionic, and non-ionic compounds.

Surfactants: Anionic

Suitable anionic surfactants for laundry compositions are well-known to those skilled in the art. Examples include primary and secondary alkyl sulphates, particularly $C_8$ to $C_{18}$ primary alkyl sulphates; alkyl ether sulphates; olefin sulphonates; alkyl xylene sulphonates; dialkyl sulphosuccinates; and fatty acid ester sulphonates. Sodium salts are generally preferred. Sodium alkyl sulphates generally make up the bulk of the anionic surfactant present in laundry compositions due to their low cost.

For hair treatment compositions examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The surfactant blends used in skin and hair compositions are generally milder than those used in laundry compositions.

The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in hair shampoo compositions of the invention include one or more of sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic surfactants for use in hair treatment compositions are the alkyl sulfates and alkyl ether sulfates. These materials have the respective formulae $R^2OSO_3M$ and $R^1O(C_2H_4O)_xSO_3M$, wherein $R^2$ is alkyl or alkenyl of from 8 to 18 carbon atoms, x is an integer having a value of from about 1 to about 10, and M is a cation such as ammonium, alkanolamines, such as triethanolamine, monovalent metals, such as sodium and potassium, and polyvalent metal cations, such as magnesium, and calcium. Most preferably for hair compositions $R^2$ has 12 to 14 carbon atoms, in a linear rather than branched chain.

Preferred anionic surfactants for use in hair treatment compositions are selected from sodium lauryl sulphate and sodium lauryl ether sulphate(n)EO, (where n is from 1 to 3); more preferably sodium lauryl ether sulphate(n)EO, (where n is from 1 to 3); most preferably sodium lauryl ether sulphate (n)EO where n=1.

Preferably the level of alkyl ether sulphate in a hair treatment composition according to the invention is from 0.5 wt % to 25 wt % of the total composition, more preferably from 3 wt % to 18 wt %, most preferably from 6 wt % to 15 wt % of the total composition.

The total amount of anionic cleansing surfactant in hair treatment (shampoo) compositions of the invention generally ranges from 0.5 wt % to 45 wt %, more preferably from 1.5 wt % to 20 wt %.

Surfactants: Nonionic

Compositions according to the present invention may contain non-ionic surfactant. Nonionic surfactants that may be used include the primary and secondary alcohol ethoxylates, especially the 08 to 020 aliphatic alcohols ethoxylated with an average of from 1 to 20 moles of ethylene oxide per mole of alcohol, and more especially the 010 to 015 primary and secondary aliphatic alcohols ethoxylated with an average of from 1 to 10 moles of ethylene oxide per mole of alcohol. Non ethoxylated nonionic surfactants include alkylpolyglycosides, glycerol monoethers, and polyhydroxyamides (glucamide).

It is preferred if the level of non-ionic surfactant is from 0 wt % to 30 wt %, preferably from 1 wt % to 25 wt %, most preferably from 2 wt % to 15 wt %, by weight of a fully formulated laundry composition comprising the particles of the invention.

Hair treatment compositions of the invention may contain non-ionic surfactant. Most preferably non-ionic surfactants are present in hair treatment compositions in the range 0 to 5 wt %.

Nonionic surfactants that can be included in hair treatment compositions of the invention include condensation products of aliphatic (C8-C18) primary or secondary linear or branched chain alcohols or phenols with alkylene oxides, usually ethylene oxide and generally having from 6 to 30 ethylene oxide groups. Alkyl ethoxylates are particularly preferred. Most preferred are alkyl ethoxylates having the formula R—(OCH2CH2)nOH, where R is an alkyl chain of C12 to C15, and n is 5 to 9.

Other suitable nonionic surfactants for use in hair treatment compositions include mono- or di-alkyl alkanolamides. Examples include coco mono- or di-ethanolamide and coco mono-isopropanolamide.

Further nonionic surfactants which can be included in compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about C5 to about C20. Preferably R represents a mean alkyl chain length of from about C8 to about C12. Most preferably the value of R lies between about 9.5 and about 10.5. G may be selected from C5 or C6 monosaccharide residues, and is preferably a glucoside. G may be selected from the group comprising glucose, xylose, lactose, fructose, mannose and derivatives thereof. Preferably G is glucose.

The degree of polymerisation of the APG, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the C10-C18 N-alkyl (C1-C6) polyhydroxy fatty acid amides, such as the C12-C18 N-methyl glucamides, as described for example in WO 92 06154 and U.S. Pat. No. 5,194,639, and the N-alkoxy polyhydroxy fatty acid amides, such as C10-C18 N-(3-methoxypropyl) glucamide.

Surfactants: Amphoteric or Zwitterionic

Amphoteric or zwitterionic surfactant can be included in an amount ranging from 0.5 wt % to about 8 wt %, preferably from 1 wt % to 4 wt % of a composition according to the invention, particularly a hair treatment composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms.

Typical amphoteric and zwitterionic surfactants for use in hair treatment compositions of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

Surfactants: Cationic

Compositions of the invention for hair treatment or laundry use may be so-called conditioners, and typically contain a conditioning surfactant. Hair conditioner compositions will typically comprise one or more conditioning surfactants which are cosmetically acceptable and suitable for topical application to hair.

Suitable conditioning surfactants include those selected from cationic surfactants, used singly or in admixture. Preferably, the cationic surfactants have the formula $N^+R^1R^2R^3R^4$ wherein $R^1$, $R^2$, $R^3$ and $R^4$ are independently ($C_1$ to $C_{30}$) alkyl or benzyl. Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl. More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (eg, oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Another example of a class of suitable cationic surfactants for use in the invention, especially in hair treatment compositions, either alone or together with one or more other cationic surfactants, is a combination of (i) and (ii) below:
(i) an amidoamine corresponding to the general formula (I):

$R^1CONH(CH_2)_mN(R^2)R^3$ in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and
(ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyl-diethylamine, stearamidoethyl-diethylamine, stearamidoethyl-dimethylamine, palmitamidopropyl-dimethylamine, palmitamidopropyl-diethylamine, palmitamidoethyl-diethylamine, palmitamidoethyl-dimethylamine, behenamidopropyl-dimethylamine, behenamidopropyl-diethylmine, behenamidoethyl-diethylamine, behenamidoethyl-dimethylamine, arachidamidopropyl-dimethylamine, arachidamidopropyl-diethylamine, arachid-amidoethyl-diethylamine, arachidamidoethyl-dimethylamine, and mixtures thereof.

Particularly preferred amidoamines useful herein are stearamidopropyl-dimethylamine, stearamidoethyl-diethylamine, and mixtures thereof.

Commercially available amidoamines useful herein include: stearamidopropyldimethylamine with tradenames LEXAMINE S-13 available from Inolex (Philadelphia Pa., USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton N.J., USA).

A protonating acid may be present. Acid may be any organic or mineral acid which is capable of protonating the amidoamine in the conditioner composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

The primary role of the acid is to protonate the amidoamine in hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate more than 95 mole % (293 K) of the amidoamine present.

In hair conditioners of the invention, the level of cationic surfactant will generally range from 0.01% to 10%, more preferably 0.05% to 7.5%, most preferably 0.1% to 5% by weight of the composition.

For laundry conditioners Dilute products typically contain up to about 8%, preferably from 2 to 8% by weight of softening active, whereas concentrated products may contain from about 8 to about 50%, preferably from 8 to 25% by weight active. Compositions of more than about 25% by weight of active are defined as "super concentrated", depending on the active system, and are also intended to be covered by the present invention. The fabric conditioning agent may, for example, be used in amounts of preferably from 2% to 30% more preferably from 5% to 25% and most preferably from 8% to 20% by weight of the composition. The fabric softening active, for use in fabric conditioner compositions of the present invention typically comprises an ester-linked triethanolamine quaternary ammonium compound (QAC).

Preferably, the QAC is derived from palm or tallow feed stocks. These feed stocks may be pure or predominantly palm or tallow based. Blends of different feed stocks may be used. The fatty acid chains of the QAC preferably comprise from 20 to 35 wt % of saturated C18 chains and from 20 to 35 wt % of monounsaturated C18 chains by weight of total fatty acid chains. In a preferred embodiment as a laundry conditioner, the fatty acid chains of the QAC comprise from 25 to 30 wt %, preferably from 26 to 28 wt % of saturated C18 chains and from 25 to 30 wt %, preferably from 26 to 28 wt % of monounsaturated C18 chains, by weight of total fatty acid chains. In a further preferred embodiment, the fatty acid chains of the QAC comprise from 30 to 35 wt %, preferably from 33 to 35 wt % of saturated C18 chains and from 24 to 35 wt %, preferably from 27 to 32 wt % of monounsaturated C18 chains, by weight of total fatty acid chains. The preferred quaternary ammonium materials for use in the present invention can be derived from feedstock having an overall iodine value of from 30 to 45, preferably from 30 to 42 and most preferably 36.

Commercial examples of suitable laundry conditioning agents include Stepantex™ UL85, ex Stepan, Prapagen™ TQL, ex Clariant, and Tetranyl™ AHT-1, ex Kao, (both di-[hardened tallow ester] of triethanolammonium methylsulphate), AT-1 (di-[tallow ester] of triethano-lammonium methylsulphate), and L5/90 (di-[palm ester] of triethanolammonium methylsulphate), both ex Kao, and Rewoquat™ WE15 (a di-ester of triethanol-ammonium methylsulphate having fatty acyl residues deriving from C10-C20 and C16-C18 unsaturated fatty acids), ex Witco Corporation. Also, quaternary ammonium actives such as Stepantex VK90, Stepantex VT90, SP88 (ex-Stepan), Ceca Noramine, Prapagen TQ (ex-Clariant), Dehyquart AU-57 (ex-Cognis), Rewoquat WE18 (ex-Degussa) and Tetranyl L190 P, Tetranyl L190 SP and Tetranyl L190 S (all ex-Kao) are suitable.

In laundry conditioners the presence of non-ionic as a floc-prevention agent, enables the formation of a thick "dilute" fabric conditioner composition, which does not flocculate upon use. Lutensol™ AT25 (BASF) based on coco chain and 25 EO groups is an example of a suitable nonoionic surfactant. Other suitable surfactants include Renex 36 (Trideceth-6), ex Uniqema; Tergitol 15-S3, ex Dow Chemical Co.; Dihydrol LT7, ex That Ethoxylate ltd; Cremophor CO40, ex BASF and Neodol 91-8, ex Shell.

Oily Conditioning Agents:

Compositions according to the present invention, especially hair treatment compositions may also comprise a dispersed, non-volatile, water-insoluble oily conditioning agent. Preferably such non-silicone conditioning oily conditioning agents are present in hair conditioner compositions.

By "insoluble" is meant that the conditioning agent is not soluble in water (distilled or equivalent) at a concentration of 0.1% (w/w), at 25° C.

Suitable oily or fatty conditioning agents are selected from hydrocarbon oils, fatty esters and mixtures thereof. Straight chain hydrocarbon oils will preferably contain from about 12 to about 30 carbon atoms. Also suitable are polymeric hydrocarbons of alkenyl monomers, such as C2-C6 alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used.

Suitable fatty esters are characterised by having at least 10 carbon atoms, and include esters with hydrocarbyl chains derived from fatty acids or alcohols, Monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as C1-C22 carboxylic acids. Preferred materials include cocoa butter, palm stearin, sunflower oil, soyabean oil and coconut oil.

The oily or fatty material is suitably present at a level of from 0.05 wt % to 10 wt %, preferably from 0.2 wt % to 5 wt %, more preferably from about 0.5 wt % to 3 wt %. "Oils" as used in this specification are distinguished from perfume materials in that perfume materials are listed as odiferous materials in Arctander's "Perfume and Flavor Materials of Natural Origin" (ISBN-10: 0-931710-36-7), or listed as odiferous materials in various databases including Flavourbase 2010, ESO 2000 (2006 update) and PMP 2001. Perfume materials are generally present as part of a complex mixture of components where each odiferous component is present at a level of below 0.5% wt of the composition as a whole. Oils present for other purposes are generally present at levels above 0.5% wt of the composition as a whole.

The laundry compositions of the invention may contain a non-cationic softening material, which is preferably an oil and more preferably an oily sugar derivative.

Fatty Alcohol:

Hair conditioners of the invention will typically also incorporate a fatty alcohol. The combined use of fatty alcohols and cationic surfactants in compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials in conditioner compositions is also advantageous in that they contribute to the overall conditioning properties of compositions of the invention.

The level of fatty alcohol in hair conditioners of the invention will generally range from 0.01 to 10%, preferably from 0.1% to 8%, more preferably from 0.2% to 7%, most preferably from 0.3% to 6% by weight of the composition. The weight ratio of cationic surfactant to fatty alcohol is suitably from 1:1 to 1:10, preferably from 1:1.5 to 1:8, optimally from 1:2 to 1:5. If the weight ratio of cationic surfactant to fatty alcohol in hair treatment compositions is too high, this can lead to eye irritancy from the composition. If it is too low, it can make the hair feel squeaky for some consumers.

The fatty alcohol may be present in laundry conditioners as a fatty complexing agent and is preferably present in an amount greater than 0.3 to 5% by weight based on the total weight of the composition. More preferably, the fatty component is present in an amount of from 0.4 to 4%. The weight ratio of the mono-ester component of the quaternary ammonium fabric softening material to the fatty complexing agent is preferably from 5:1 to 1:5, more preferably 4:1 to 1:4, most preferably 3:1 to 1:3, e.g. 2:1 to 1:2.

Suspending Agent:

Preferably an aqueous composition of the invention further comprises a suspending agent and/or viscosity enhancer.

Examples of suitable materials include: natural gums such as carrageenan, xanthan gum, gum arabic, gum tragacanth and guar gum and derivatives thereof such as hydroxypropyl guar and guar hydroxypropyl trimoniumchloride; inorganic thickeners such as colloidal magnesium aluminium silicate (Veegum), finely divided silica, natural clays such as bentonite and synthetic clays such as the synthetic hectorite available as Laponite (ex Laporte Industries Ltd);

Perferred are materials selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof.

Ethylene glycol distearate and polyethylene glycol 3 distearate are preferred long chain acyl derivatives, since these impart pearlescence to the composition.

Polyacrylic acid is available commercially as Carbopol 420, Carbopol 488 or Carbopol 493.

Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent will generally be present in a hair treatment composition of the invention at levels of from 0.1% to 10%, preferably from 0.5% to 6%, more preferably from 0.9% to 4% by total weight of suspending agent based on the total weight of the composition.

Silicone:

The compositions of the invention can contain, emulsified droplets of a silicone. In hair treatment composition these give enhancing conditioning performance.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final composition) is typically at least 10,000 cst at 25 oC the viscosity of the silicone itself is preferably at least 60,000 cst, most preferably at least 500,000 cst, ideally at least 1,000,000 cst. Preferably the viscosity does not exceed 109 cst for ease of formulation.

Emulsified silicones for use in the compositions of the invention will typically have an average silicone droplet size in the composition of less than 30, preferably less than 20, more preferably less than 10 micron, ideally from 0.01 to 1 micron. Silicone emulsions having an average silicone droplet size of 0.15 micron are generally termed microemulsions.

Emulsified silicones for use in the compositions of the invention will typically have an size in the composition of less than 30, preferably less than 20, more preferably less than 15. Preferably the average silicone droplet is greater than 0.5 micron, more preferably greater than 1 micron, ideally from 2 to 8 micron.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in compositions of the invention, especially hair treatment compositions are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone".

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The total amount of silicone is preferably from 0.01 wt % to 10% wt of the total composition more preferably from 0.1 wt % to 5 wt %, most preferably 0.5 wt % to 3 wt % is a suitable level.

Cationic Polymers:

Cationic polymers are preferred ingredients in hair-treatment compositions of the invention for enhancing performance.

Suitable cationic polymers may be homopolymers which are cationically substituted or may be formed from two or more types of monomers. The weight average ($M_w$) molecular weight of the polymers will generally be between 100 000 and 2 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo- and copolymers of unsaturated carboxylic acids having from 3 to 5 carbon atoms, (as described in U.S. Pat. No. 4,009,256);
cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include monomers of the formula:

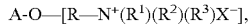

A-O—[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR 014, JAGUAR 015, JAGUAR 017 and JAGUAR 016 Jaguar CHT and JAGUAR 0162.

Mixtures of any of the above cationic polymers may be used.

Cationic polymer will generally be present in a hair shampoo composition of the invention at levels of from 0.01 to 5%, preferably from 0.05 to 1%, more preferably from 0.08 to 0.5% by total weight of cationic polymer based on the total weight of the composition.

The amount of polymer used in the laundry compositions of the invention is suitably from 0.001 to 0.5 wt %, preferably from 0.005 to 0.4 wt %, more preferably from 0.05 to 0.35 wt % and most preferably from 0.1 to 0.25 wt %, by weight of the total composition. An example of a preferred polymer is Flosoft 270LS ex SNF.

Minors:

As further optional components for inclusion in compositions according to the invention may be mentioned the following conventional adjunct materials known for use in cosmetic compositions: emulsifiers, humectants, suspending agents, rheology modifiers, pearlescing agents, opacifiers, salts, perfumes, buffering agents, colouring agents, emollients, moisturisers, foam stabilisers, sunscreen materials, antimicrobial agents, preservatives, antioxidants, and natural oils and extracts. Some or all of these may be present in the bulk of the composition as well as some being present as a benefit agent in the befit agent delivery particles.

Shading Dye:

Optional shading dyes can be used in the hair and laundry compositions of the present invention. Preferred dyes appear violet or blue. The shading dyes can perform a variety of functions relating to the yellowing of the substrate. For example in laundry compositions any unsaturated quaternary ammonium compounds are subject to some degree of UV light and/or transition metal ion catalysed radical auto-oxidation, with an attendant risk of yellowing of fabric and shading dye reduces the risk of yellowing from this source.

Different shading dyes give different levels of colouring. The level of shading dye present in the compositions of the present invention depends, therefore, on the type of shading dye. Preferred overall ranges, suitable for the present invention are from 0.00001 to 0.1 wt %, more preferably 0.0001 to 0.01 wt %, most preferably 0.0005 to 0.005 wt % by weight of the total composition.

In order that the present invention may be further understood and carried forth into practice it will be further described with reference to the following examples. In the examples, as in the rest of the specification, all percentages are by weight unless otherwise specified.

EXAMPLES

Example 1

Deposition Performance of particles on Fabrics

1-Ethyl-3-(3-dimethylaminopropyl) carbodiimide hydrogen chloride (EDAC) was obtained from Alfa Aesor and all other chemicals obtained from Sinopharm Chemical Reagent Co., Ltd.

a) Synthesis of Carboxyl Functional Polystyrene Particle (3.6 µm)

Carboxyl-functionalized polystyrene particles were synthesized via dispersion copolymerization. 500 mL three neck flask was charged with 140 mL ethanol and 12.0 mL DI water containing 38.0 g styrene, 1.4 g acrylic acid and 3.0 g poly (N-vinylprrolidiene). A nitrogen blanket and stirring rate of 500 rpm were maintained. This solution was deoxygenated by bubbling with nitrogen for 1.0 hr. After thorough deoxygenation, the temperature was increased to 70° C. and 6.0 g AIBN added to this solution. The reaction was kept at 70° C. for 20 hrs. After being cooled to room temperature, the latex was centrifuged at 10000 rpm for 15 minutes and the supernatant decanted off. The latex particles were re-dispersed in 100 mL ethanol, centrifuged at 10000 rpm for 15 minutes and the supernatant decanted off. The latex was then re-dispersed in ethanol and centrifuged again, the supernatant decanted off and the carboxyl functional polyester particle collected.

b) Purification of Latex Particles

The carboxyl functional polyester particle (3.6 µm) was purified via the following procedure.

Step 1: 1.0 mL latex was diluted with 0.5 mL pH 7.01 buffer and centrifuged at 10000 rpm for 15 minutes. The wash in pH 7 buffer was repeated once.

Step 2: The supernatant was decanted off and the latex re-dispersed in DI water. The solution was centrifuged again at 10000 rpm for 15 minutes and the supernatant decanted off. The wash in de-ionised water was also repeated once.

c) Grafting of Polysaccharides onto Latex Particles (3.6 µm) Via EDAC Coupling

Direct chemical coupling with EDAC coupling was used for graft of Polysaccharide onto PS particles.

The above purified latex was re-dispersed in 500 mL DI water with solid content of 5.5% (w/w). 25 mL de-ionised water and 0.28 g EDAC was added into 4.57 mL above purified latex (5.5% solid content) and the resulted mixture stirred at 25° C. for 3 hours. Then the latex was centrifuged at 1000 rpm for 10 minutes and purified with pH7 buffer and de-ionised water according to Step 1 and 2 shown in Example 10b. Then the latex was re-dispersed in 20 mL de-ionised water.

Polysaccharide solution (0.9 g/L) was prepared separately and stirred at 25° C. for 3 hours to ensure complete dissolution of any dispersed gel materials. 10 mL EDAC modified PS particle was mixed with 5.6 or 66.7 mL polysaccharide solution as feed ratio of polysaccharide to PS particle 0.05:1 or 0.6:1, respectively. The mixture was then stirred at 45° C. for 24 hours. After that, the latex was centrifuged at 10000 rpm for 15 minutes and purified in pH7 buffer and de-ionised water again according to 1 and 2 shown in Example 10b. At last the latex was re-dispersed in 10 mL de-ionised water to give a final latex dispersion of polysaccharide grafted particles with solids of 1.0% (w/w).

d) Preparation of Comparative Example (Polystyrene Latex without Surface Attached Polysaccharide)

A comparative (control) sample without any addition of polysaccharide was prepared according to the identical procedure shown in Example 1a. The final solid content of latex was adjusted to 1.0% (w/w).

The deliveries of polystyrene latex (3.6 µm, with or without polysaccharides) were assessed with Sodium dodecylbenzenesulphonate (LAS) and Synperonic A7 as surfactant stock using the constant temperature shaking apparatus (model THZ platform, supplied by Shanghai Jing Hong laboratory instrument Co., Ltd.).

e) Preparation of Stock Solutions

Surfactant stock was prepared by dissolving LAS (5.0 g) and Synperonic A7 (5.0 g) in de-ionised water to a total of 1.0 litre. The surfactant concentration of final solution is 10 g/L (50% LAS, 50% Synperonic A7). Base buffer stock was prepared by dissolving sodium carbonate (7.546 g) and sodium bicarbonate (2.419 g) in de-ionised water to a total of 1.0 litre. The base buffer concentration is 0.1 M.

f) Bottle Wash Procedure

The constant temperature shaking apparatus was utilized to simulate wash procedure for deposition performances assessment. The typical procedure was described as below.

55 mL model wash liquor (1.0 g/L surfactant and 0.01 M base buffer) containing 600 ppm polystyrene latex (3.6 μm) with or without grafted polysaccharide was prepared in a 120 mL bottle and a 5.0 mL aliquot taken out for absorbance recording at 400 nm. This absorbance value represents 100% particles in the wash solution prior to the bottle wash process.

A piece (20×20 cm) of unfluoresced knitted polyester (around 5.0 g) or three pieces (10×10 cm) of unfluoresced cotton fabric (totally around 4.5 g) were then placed into the bottle and the bottle sealed. The shaker bath was heated to 40° C. and the bottle clamped into it and shaken at 125 rpm for 30 minutes to simulate the main wash. The fabrics were then removed and wrung by hand and a 10.0 mL aliquot of the main wash solution taken out for absorbance recording at 400 nm. The amount of adsorbed polystyrene latex on fabric could be determined by turbidity difference before/after main wash stage.

The bottle was then thoroughly washed. Wrung fabrics were put back to the bottles and 50 mL of DI water added. The bottle was shaken at 40° C. for 10 minutes at 125 rpm to simulate a rinse procedure. The fabric were then removed and wrung by hand again. A 10.0 mL aliquot of the rinse solution was taken out for absorbance recording at 400 nm. The loss amount of absorbed polystyrene latex from fabric in rinse 1 stage could be determined according to turbidity. The rinse procedure was repeated once and the loss amount of polystyrene latex from fabric in rinse 2 stage could be determined.

The deposition results of latex particle model systems onto polyester are illustrated in the following table:

| Material & Supplier | Visc | Mw | Graft [a] | Dep. wash | Dep. rinse |
|---|---|---|---|---|---|
| Hydroxyethyl Cellulose (TCI) H0242 (Comparative) | 200-300 (2%, 20° C.) | 380k [c] | — | 39% | 19% |
| Hydroxyethyl Cellulose (TCI) H0418 (Comparative) | 4500-6500 (2%, 20° C.) | 557k [c] | — | 57% | 37% |
| Hydroxyethyl Cellulose (TCI) H0392 (Comparative) | 800-1500 (2%, 20° C.) | 1384k [c] | — | 44% | 23% |
| Hydroxyethyl Cellulose (Ashland) 250HR (Comparative) | 1900 (2%, 20° C.) | 1559k [c] | — | 44% | 33% |
| Hydroxymethyl hydroxyethyl cellulose (Ashland) Polysurf 67 (Comparative) | 8000 (1%, 25° C.) | — | — | 48% | 27% |
| Hydroxymethyl hydroxyethyl cellulose (Ashland) Pluss330 (Comparative) | 490 (1%, 25° C.) | — | 27.8 | 35% | 21% |
| Ethyl cellulose (Ashland) N7 (Comparative) | 7 (5%, 25° C.) [b] | — | — | 26.0% | 7.7% |
| Ethyl cellulose (Ashland) N50 (Comparative) | 50 (5%, 25° C.) [b] | — | — | 32.1% | 10.5% |
| Ethyl cellulose (Ashland) N14 (Comparative) | 14 (5%, 25° C.) [b] | — | — | 32.7% | 12.4% |
| Cellulose Acetate Butyrate (Aldrich) (Comparative) | — | 30k | — | 23% | −3% |
| Carboxymethyl cellulose (TCI) C0045 (Comparative) | — | ≈130k DP = 500 | — | 52% | 30% |
| Carboxymethyl cellulose (TCI)C0603 (Comparative) | — | ≈273k DP = 1050 | 27% | 39% | 11% |
| Starch (Alfa Aesar) (comparative) | — | — | 22% | 46% | 31% |
| Carrageenan (TCI) C1804 (comparative) | — | — | — | 33% | 16% |
| Carrageenan (TCI)C1805 (comparative) | — | — | — | 26% | 11% |
| Pectin (TCI) P0024 (comparative) | — | — | — | 37% | 19% |
| Tamarind gum (TCI) T0909 (comparative) | — | — | — | 55% | 36% |
| Xanthan gum (TCI) X0048 (comparative) | — | — | — | 32% | 14% |
| Gum Arabic (Sinopharm Chemical Reagent Co., Ltd) (comparative) | 60-170 (1%, 25° C.) | — | — | 35% | 14% |
| Dextran (Sigma) D-200000 | — | 200k | 4% | 69% | 50% |
| Dextran (Sinopharm Chemical Reagent Co., L.td) D-40000 | — | 40k | 10% | 80% | 63% |
| Dextran (Herochem Biology& Chemical Reagent Co., Ltd) D-20000 | — | 20k | 12% | 80% | 68% |
| Dextran (Aladin Reagent ) D-10000 | — | 10k | 22% | 70% | 54% |
| Dextran (Sigma) D-6000 | — | 6k | 59% | 62% | 42% |

[a] Feed ratio of polysaccharide to PS particle is 0.6:1.
[b] Solvent is 80% toluene and 20% ethanol. For all other viscosity data, the solvent is water.
[c] Lab analysis results.

Example 2

Deposition of Particles on Cotton

The following results were obtained when the latex particles of example 1 were deposited onto cotton:

| Material & Supplier | Visc | Mw | Graft [a] | Dep. wash | Dep. rinse |
|---|---|---|---|---|---|
| Original particle (no delivery aid) | — | — | — | 52.4% | 43.9% |
| Hydroxyethyl Cellulose (Ashland) 250HR (comparative) | 1900 (2%, 20° C.) | 1559k [b] | — | 72.5% | 65.7% |
| Dextran (Sigma) D-200000 | — | 200k (190k [b]) | — | 73.6% | 60.8% |
| Dextran (Nanjing Duly Biotech Co., Ltd) T70 | — | 70k (73k [b]) | 76% | 70.0% | 57.1% |
| Dextran (Herochem Biology & Chemical Reagent Co., Ltd) D-20000 | — | 20k (18k [b]) | 88% | 52.8% | 43.8% |

[a]: feed ratio of polysaccharide to PS particle is 0.05;
[b] Lab analysis results The table below shows some consolidated results for Example 1 and 2, in which the deposition percentage is recorded after the rinse for both polyester and cotton. It can be seen that particles according to the present invention (those using dextrans) show excellent deposition on both polyester and cotton, but that a comparative example (using HEC) gives good deposition on cotton but fails to give good deposition on polyester.

| Material & Supplier | Dep. Polyester | Dep. Cotton |
|---|---|---|
| Original particle (no delivery aid - control) | — | 43.9% |
| Dextran (Sigma) D-200000 | 50% | 60.8% |
| Dextran (Herochem Biology & Chemical Reagent Co., Ltd) D-20000 | 68% | 43.8% |
| Hydroxyethyl Cellulose (Ashland) 250HR (comparative) | 33% | 65.7% |

Example 3

Surface Attachment of Dextran onto Perfume Encapsulates Via Melamine Formaldehyde Shell Formation The pre-formed melamine formaldehyde perfume encapsulates were 15 micron in size and obtained from Givaudan Limited. The particle solids were 41.6 wt % and perfume solids were 28.0 wt % respectively. The dextran was supplied by Aldrich (catalogue number 31398).

The following procedure outlines the synthetic modification to attach dextran to the surface via the formation of additional melamine formaldehyde (MF) shell:

a) Pre-polymer Preparation

To a 100 ml conical flask was add 19.5 g formalin (37 wt % aqueous formaldehyde) and 44.0 g water. The pH of the solution was adjusted to 8.9 using 0.3 g of 5 wt % aqueous sodium carbonate. 10 g of melamine and 0.64 g of sodium chloride were added and the mixture stirred for 10 minutes at room temperature. The mixture was heated to 65° C. and stirred until it became clear. This mixture is hereinafter referred to as "pre-polymer (1)".

b) Dextran Attachment to Melamine Formaldehyde Perfume Encapsulates

A 1 wt % solution of dextran was prepared by dissolving 1.0 g of dextran in 99.0 g deionised water by shaking overnight on an orbital shaker (VWR Standard 5000 Shaker at number 4 setting). 50 g of this dextran solution was transferred to a 250 ml round bottomed flask fitted with overhead stirrer and condenser. 23.6 g of melamine formaldehyde encapsulate slurry (41.6 wt % particle solids) was added and the mixture heated to 75° C. with stirring. 0.9 g of a freshly prepared pre-polymer (1) solution was added and the pH adjusted to 4.1, using approximately 2 g of 10 wt % formic acid aqueous solution. The mixture was then left to stir, at 75° C. for 2 hours. The solution was then cooled and adjusted to pH 7 using approximately 6 g of 5 wt % sodium carbonate aqueous solution.

A final dispersion (approximately 100 g) consisting of 10 wt % encapsulate solids containing an additional 2 wt % melamine formaldehyde shell and 5 wt % (based on final particle weight) of dextran was obtained.

Example 4

Deposition to Hair from Shampoo and Conditioners

The deposition to hair from shampoo and conditioners of the dextran attached to the perfume encapsulate (in Example 3) was assessed as follows:

a) Preparation of Hair Care Formulations

Model shampoo formulations were prepared by adding 12% active SLES, 1.6% active CAPB and 1% active Sodium Chloride to deionised water. From this, formulations containing 1% active MF encap with or without grafted polysaccharide were prepared.

Model hair conditioner formulations were prepared by adding Lactic Acid 0.38%, Lexamine S-13 1.25%, Genamin BTLF 0.87%, Lanette S3 5%, Nipagin M 0.2%. From this formulations containing 1% active MF encap with or without grafted dextran were prepared.

b) Hair Wash, Extraction and Analysis Procedure

Switches of dark brown European hair (DBE) 2" in length, weighing 0.3 g were initially base washed in 14% SLES solution. Then a standard wash protocol was used for shampoo or conditioner formulations. Both root and distal hair switches were tested.

Shampoo Treatment: Using a tap with water flowing at 35-40 deg C., flow rate 3-4 litres per minute, the switch was thoroughly wet and excess water shaken off. 0.1 g of shampoo per g of hair was applied along the length of each switch and agitated by rubbing between the hands for 30 seconds. The switches were then rinsed with warm running water for 30 seconds. The excess water was shaken off and the switch left to dry.

Conditioner Treatment: Using a tap with water flowing at 35-40 deg C., flow rate 3-4 litres per minute, the switch was thoroughly wet and excess water shaken off. 0.2 g of conditioner per g of hair was applied along the length of each switch and agitated by rubbing between the hands for 1 minute. The switches were then rinsed with warm running water for 1 minute. The excess water was shaken off and the switch left to dry.

Five repetitions of switches were washed per treatment for reproducibility.

When dry, each switch was placed into a glass vial and 2 mls of Ethanol added to extract any deposit. The vials were bottle rolled for 2 hours. From each vial 100 ul aliquots were taken and placed into a 96-well plate. The plate was then measured for fluorescence on a high throughput Thermo Varioskan Flash Fluorescence Spectrometer.

The efficiency of deposition of MF encapsulates could be determined by comparison to a calibration of fluorescence versus concentration and the expected fluorescence for full deposition.

The deposition results of MF encaps onto hair are illustrated in the following table:

| Material | Shampoo Deposition Efficiency (%) | | Conditioner Deposition Efficiency (%) | |
|---|---|---|---|---|
| | Root | Distal | Root | Distal |
| Unmodified encapsulate | 3 | 3 | 3 | 0.5 |
| Dextran modified encapsulate | 18 | 13 | 12 | 10 |

The results show the surface attachment of dextran to the perfume encapsulate enhances the delivery to hair from both shampoo and conditioner formulations.

The invention claimed is:

1. A benefit agent delivery particle comprising:
   at least one delivery aid and
   an aminoplast polymer;
   wherein the at least one delivery aid comprises dextran;
   wherein the dextran is located at the outer surface of the particle; and
   wherein the dextran is an α-D-1,6-glucose-linked glucan with 1-3-branch linkages.

2. A particle according to claim 1 wherein the dextran has a molecular weight above 5 kD.

3. A particle according to claim 1 which comprises a perfume.

4. A particle according to claim 1 which comprises a core and a shell.

5. A composition comprising:
   a) a particle according to claim 1, and,
   b) an enzyme selected from the group consisting of hemicellulase, cellulase, polygalacturonase, xylanase, pectinase, mannanase, pectate lyase, ligninase, pullulanase, pentosanase, arabinosidase, hyaluronidase, chondroitinase, laccase, glycosylhydrolase, amylases, and mixtures thereof.

6. A laundry treatment composition comprising:
   a) a particle according to claim 1,
   b) at least one anionic or non-ionic surfactant, and,
   c) an enzyme selected from the group consisting of cellulase, mannanase and mixtures thereof.

7. A laundry treatment composition according to claim 6 wherein the composition is a liquid or gel.

8. A hair treatment composition comprising:
   a) a particle according to claim 1,
   b) at least one anionic or non-ionic surfactant.

9. A process comprising:
   a) encapsulating a perfume oil using emulsion polymerization to form core-shell particles, and,
   b) forming a further polymer layer on the outer surface of the core shell-particles in the presence of dextran to form the benefit agent delivery particles according to claim 1.

10. A particle according to claim 2, wherein the dextran has a molecular weight above 20 kD.

* * * * *